United States Patent
Watanabe et al.

(10) Patent No.: US 11,959,877 B2
(45) Date of Patent: Apr. 16, 2024

(54) GAS SENSOR

(71) Applicant: NGK INSULATORS, LTD., Aichi (JP)

(72) Inventors: Yusuke Watanabe, Nagoya (JP); Takayuki Sekiya, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 695 days.

(21) Appl. No.: 17/128,361

(22) Filed: Dec. 21, 2020

(65) Prior Publication Data

US 2021/0109058 A1 Apr. 15, 2021

Related U.S. Application Data

(63) Continuation of application No. PCT/JP2019/025045, filed on Jun. 25, 2019.

(30) Foreign Application Priority Data

Jun. 28, 2018 (JP) ................. 2018-122843

(51) Int. Cl.
*G01N 27/407* (2006.01)
*G01N 1/24* (2006.01)
(Continued)

(52) U.S. Cl.
CPC ............... *G01N 27/41* (2013.01); *G01N 1/24* (2013.01); *G01N 27/4071* (2013.01); *G01N 33/0006* (2013.01); *G01R 19/0092* (2013.01)

(58) Field of Classification Search
CPC .... G01N 27/41; G01N 27/24; G01N 27/4071; G01N 27/4065; G01N 33/0006; G01R 19/0092

See application file for complete search history.

(56) References Cited

U.S. PATENT DOCUMENTS

| | | |
|---|---|---|
| 2012/0097553 A1 | 4/2012 | Classen et al. |
| 2014/0102170 A1 | 4/2014 | Kato et al. |
| 2015/0276659 A1 | 10/2015 | Sekiya et al. |

FOREIGN PATENT DOCUMENTS

| | | |
|---|---|---|
| JP | 2015-200643 A | 11/2015 |
| WO | 2013/005491 A1 | 1/2013 |

OTHER PUBLICATIONS

International Preliminary Report on Patentability received in corresponding International Application No. PCT/JP2019/025045 dated Jan. 7, 2021.

(Continued)

*Primary Examiner* — Alexander S Noguerola
(74) *Attorney, Agent, or Firm* — MATTINGLY & MALUR, PC

(57) ABSTRACT

In a gas sensor, oxygen pumping control is performed to pump oxygen from the surroundings of an outer side pump electrode into the surroundings of a reference electrode. In addition, during execution of the oxygen pumping control, a pump current Ip2 is measured when oxygen originating from NOx is pumped out from the surroundings of a measurement electrode so that a voltage V2 reaches a target voltage V2*. Then, the NOx concentration of a measurement-object gas is calculated based on Ip2. In the gas sensor, the NOx concentration is corrected based on DVref which is the difference between Vref1 and Vref2, wherein Vref1 is the voltage across the reference electrode and the outer side pump electrode when the oxygen pumping control is not performed, and Vref2 is the voltage across the reference electrode and the outer side pump electrode when the oxygen pumping control is performed.

5 Claims, 7 Drawing Sheets

(51) Int. Cl.
    *G01N 27/41*     (2006.01)
    *G01N 33/00*     (2006.01)
    *G01R 19/00*     (2006.01)

(56) References Cited

OTHER PUBLICATIONS

International Search Report of PCT/JP2019/025045 dated Sep. 24, 2019.

GAS SENSOR

CROSS-REFERENCE TO RELATED APPLICATION

This application is a continuation application of PCT/JP2019/025045, filed on Jun. 25, 2019, which claims the benefit of priority of Japanese Patent Application No. 2018-122843, filed on Jun. 28, 2018, the entire contents of which are incorporated herein by reference.

BACKGROUND OF THE INVENTION

1. Field of the Invention

The present invention relates to a gas sensor.

2. Description of the Related Art

A gas sensor has been known which detects a specific gas concentration such as NOx in a measurement-object gas, such as exhaust gas of automobiles. For instance, PTL 1 describes a gas sensor including: a laminated body in which multiple oxygen ion conductive solid electrolyte layers are laminated; a reference electrode which is provided inside the laminated body and into which a reference gas (for instance, air) is introduced; a measurement electrode provided in a measurement-object gas flow section inside the laminated body; and a measurement-object gas side electrode provided in a portion of the laminated body, the portion being exposed to the measurement-object gas. The gas sensor measures a current when oxygen originating from a specific gas is pumped out from the surroundings of the measurement electrode so that the voltage across the reference electrode and the measurement electrode reaches a target voltage, and calculates the concentration of the specific gas in the measurement-object gas based on the current. In addition, the gas sensor causes current (oxygen pumping current) to flow between the reference electrode and the measurement-object gas side electrode to pump oxygen into the surroundings of the reference electrode. When the oxygen concentration of the reference gas in the surroundings of the reference electrode is temporarily reduced, the reduction in the oxygen concentration can be compensated by pumping oxygen into the surroundings of the reference electrode in this manner, and reduction in the accuracy of detection of a specific gas concentration is decreased.

CITATION LIST

Patent Literature

PTL 1: Japanese Unexamined Patent Application Publication No. 2015-200643

SUMMARY OF THE INVENTION

However, when oxygen in the surroundings of the measurement-object gas side electrode is pumped in the surroundings of the reference electrode, the accuracy of detection of a specific gas concentration in the measurement-object gas may be reduced. The reduction in the accuracy of detection is noticeable when the reference electrode degrades with time, and the resistance of the reference electrode is increased.

The present invention has been devised to solve the problem described above, and it is the main object to improve the accuracy of detection of a specific gas concentration in the measurement-object gas.

The present invention adopts the following device to achieve the main object mentioned above.

A gas sensor of the present invention includes:

a laminated body which has a plurality of laminated oxygen ion conductive solid electrolyte layers and is inwardly provided with a measurement-object gas flow section which introduces and allows a measurement-object gas to flow;

a reference electrode which is disposed inwardly of the laminated body, and to which a reference gas is introduced, the reference gas serving as a reference for detection of a specific gas concentration in the measurement-object gas;

a measurement electrode provided on an inner circumferential surface of a measurement chamber of the measurement-object gas flow section;

a measurement-object gas side electrode provided in a portion of the laminated body, the portion being exposed to the measurement-object gas;

a control device that performs oxygen pumping control to pump oxygen from surroundings of the measurement-object gas side electrode into surroundings of the reference electrode; and a calculation device that, during execution of the oxygen pumping control, measures a pump current for concentration detection when oxygen originating from the specific gas is pumped out from surroundings of the measurement electrode so that a voltage across the reference electrode and the measurement electrode reaches a target voltage, and calculates the specific gas concentration of in the measurement-object gas based on the pump current for concentration detection, wherein the calculation device corrects the specific gas concentration in the measurement-object gas based on a difference between a first base voltage and a second base voltage, the first base voltage across the reference electrode and the measurement-object gas side electrode when the oxygen pumping control is not performed, the second base voltage across the reference electrode and the measurement-object gas side electrode when the oxygen pumping control is performed.

The gas sensor performs oxygen pumping control to pump oxygen from the surroundings of the measurement-object gas side electrode into the surroundings of the reference electrode. For instance, when the measurement-object gas enters the surroundings of the reference electrode, the oxygen concentration of the reference gas is reduced. However, the reduction in the oxygen concentration can be prevented by performing oxygen pumping control. Also, during execution of the oxygen pumping control, the gas sensor measures a pump current for concentration detection when oxygen originating from a specific gas is pumped out from the surroundings of the measurement electrode so that the voltage across the reference electrode and the measurement electrode reaches a target voltage, and calculates a specific gas concentration of the measurement-object gas based on the pump current for concentration detection. The voltage across the reference electrode and the measurement electrode includes a voltage drop, in addition to an electromotive force based on the oxygen concentration difference between the surroundings of the measurement electrode and the surroundings of the reference electrode, the voltage drop being obtained by multiplying the resistance of the reference electrode by the current which flows through the reference electrode at the time of oxygen pumping control. The voltage drop is probably equal to the difference between a first base voltage and a second base voltage, the first base voltage across the reference electrode and the measurement-object gas side electrode when the oxygen pumping control is not performed, the second base voltage across the reference electrode and the measurement-object gas side electrode when the oxygen pumping control is performed. Here, the specific gas concentration of the measurement-object gas is corrected based on the difference, thus it is possible to prevent reduction in the accuracy of detection of the specific gas concentration due to degradation with time.

In the gas sensor of the present invention, the oxygen pumping control device performs the oxygen pumping control by applying a voltage repeatedly turned ON and OFF across the measurement-object gas side electrode and the reference electrode, and the calculation device may measure the pump current for concentration detection and the second base voltage during a period in which the repeatedly turned ON and OFF voltage is OFF in the oxygen pumping control. In this manner, it is possible to reduce the effect of the voltage used for the oxygen pumping control on the measurement of the pump current for concentration detection. In this case, the calculation device may measure the pump current for concentration detection and the second base voltage at a timing in a period in which the repeatedly turned ON and OFF voltage is OFF in the oxygen pumping control, the timing immediately before the voltage is set ON next. In this manner, it is possible to further reduce the effect of the voltage used for the oxygen pumping control on the measurement of the pump current for concentration detection.

In the gas sensor of the present invention, when measuring the pump current for concentration detection, the calculation device may correct the target voltage used in the past based on the difference amount between a difference of the first base voltage and the second base voltage at the present and a difference of the first base voltage and the second base voltage in the past, and may measure the pump current for concentration detection when oxygen originating from the specific gas is pumped out from the surroundings of the measurement electrode so that the target voltage after being corrected is achieved. The difference amount is probably the difference between the voltage drop at the present and the voltage drop in the past. In other words, it may be stated that the difference amount is a voltage that reflects the amount of resistance change when the reference electrode degrades with time from the past to the present and the resistance of the reference electrode changes. Thus, the target voltage can be appropriately set by correcting the target voltage based on the difference amount. It is to be noted that in the "past" may be the previous time or may be the first time, for instance.

In the gas sensor of the present invention, the calculation device may further correct the specific gas concentration in the measurement-object gas based on the amount of change with time in the thermal electromotive force. In this way, it is possible to prevent reduction in the accuracy of detection of the specific gas concentration due to elapse of time.

DETAILED DESCRIPTION OF THE INVENTION

Figure 1:
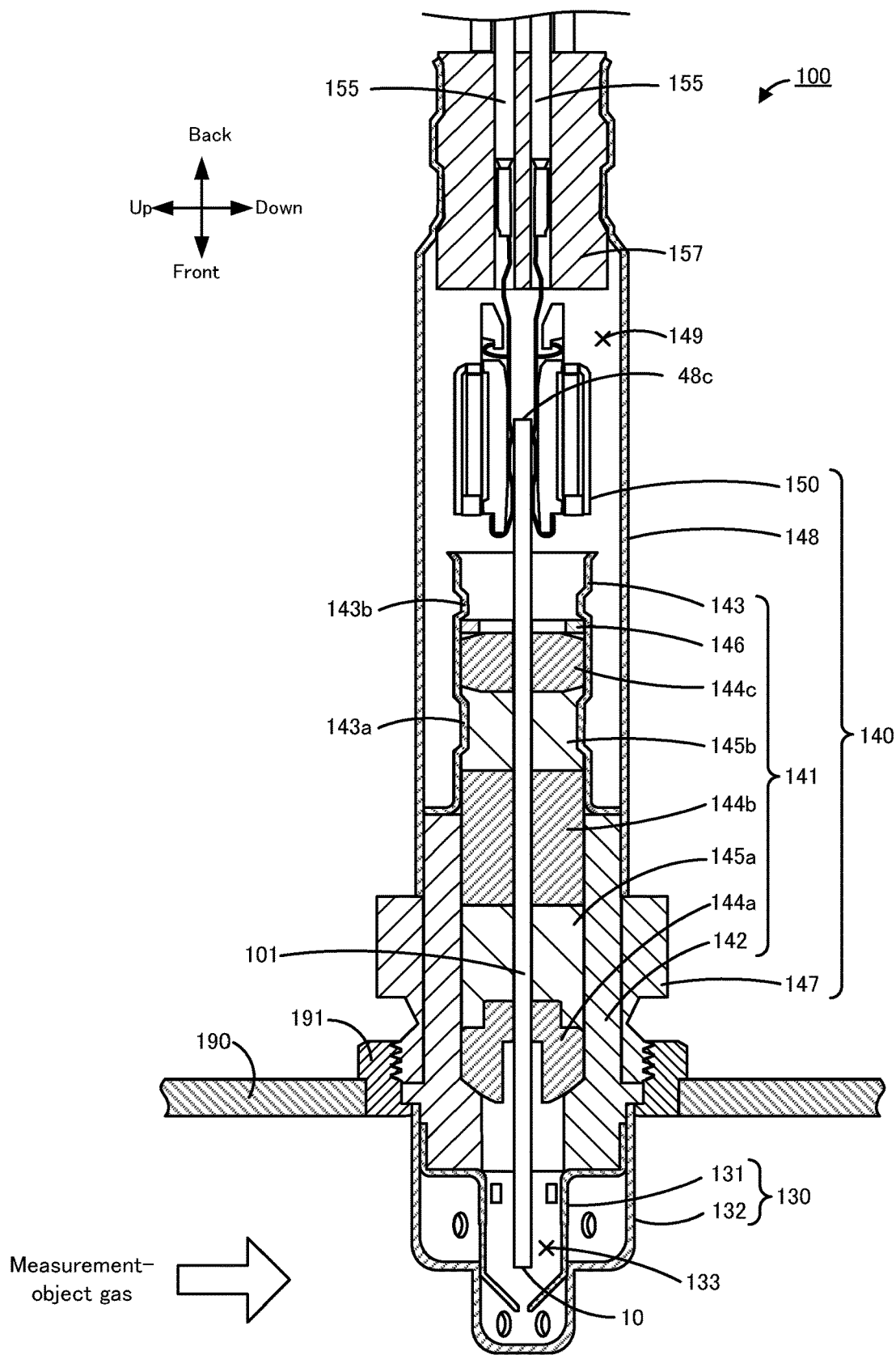
FIG. 1 is a vertical cross-sectional view of a gas sensor 100.
Figure 2:
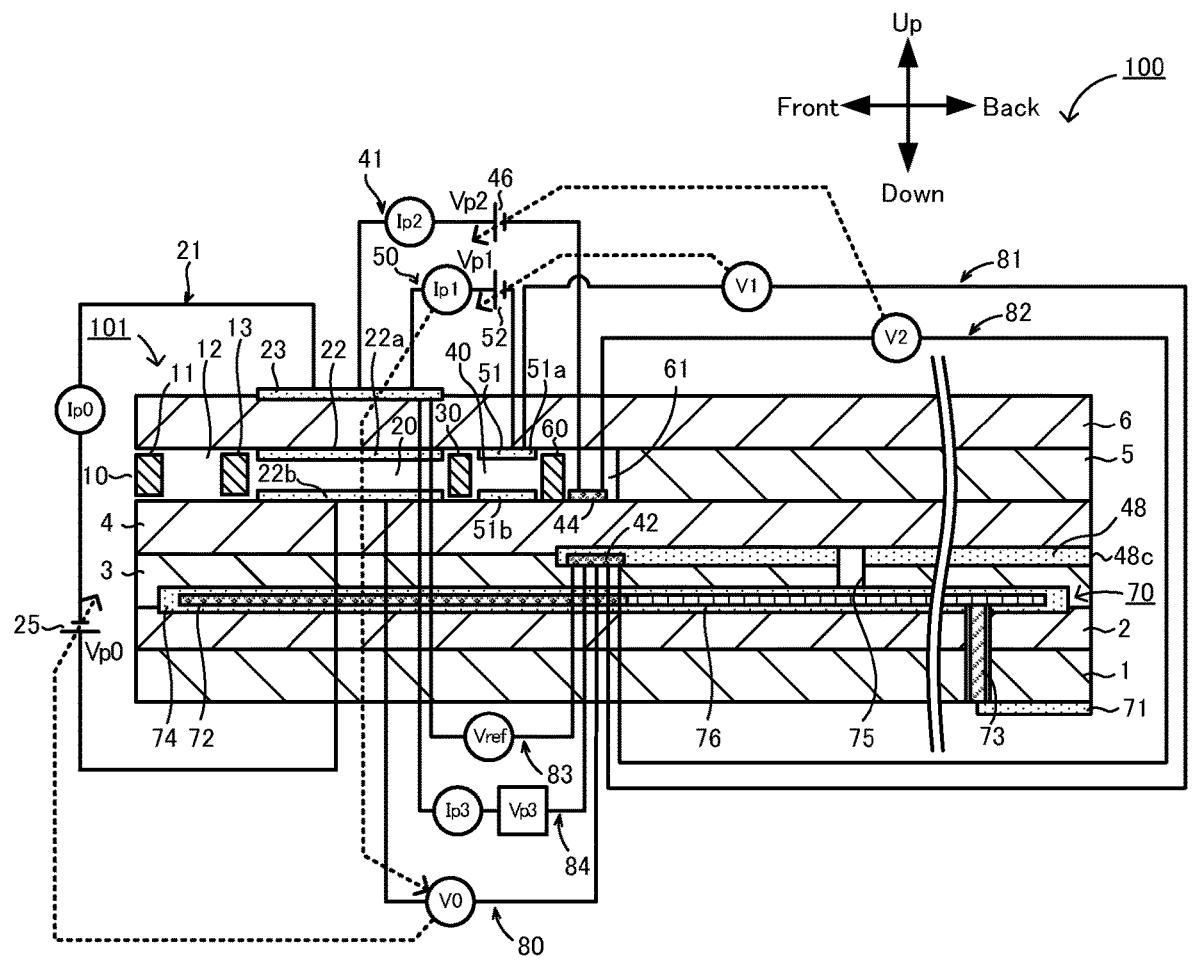
FIG. 2 is a cross-sectional schematic view schematically illustrating an example of a configuration of a sensor element 101.
Figure 3:
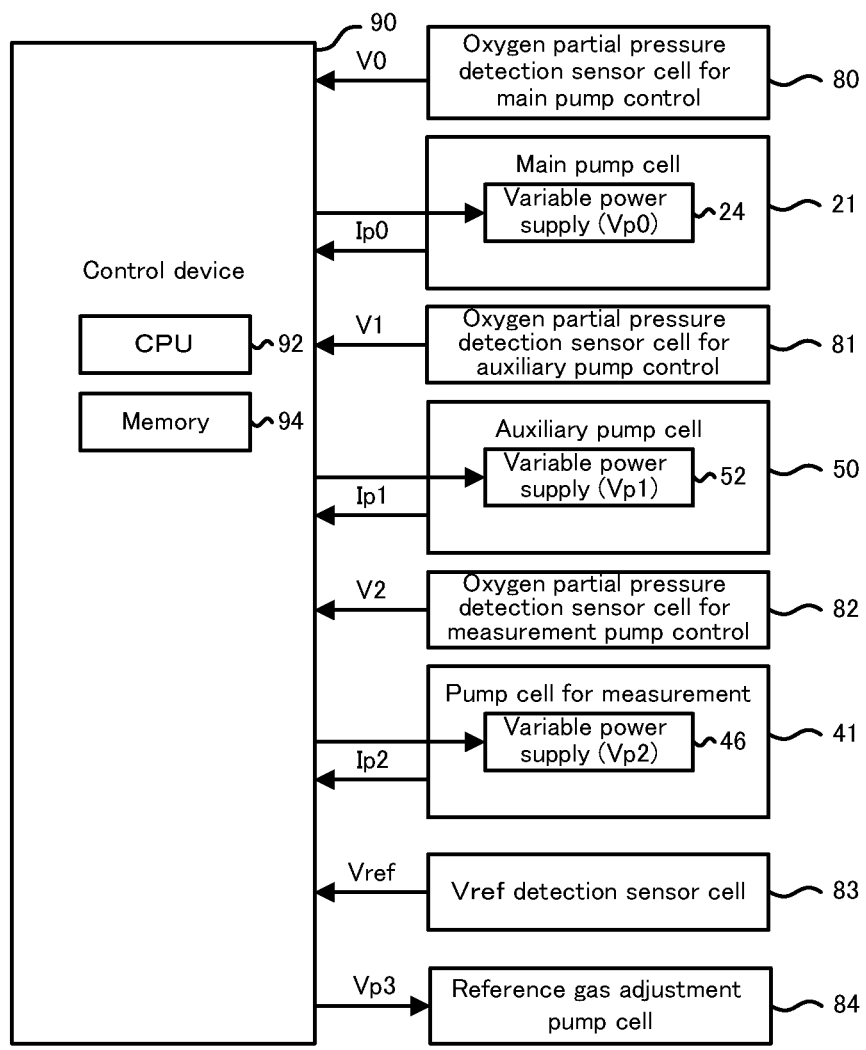
FIG. 3 is a block diagram illustrating an example of a control device 90.

Next, an embodiment of the present invention will be described with reference to the drawings. FIG. 1 is a vertical cross-sectional view of a gas sensor 100 which is an embodiment of the present invention. FIG. 2 is a cross-sectional schematic view schematically illustrating an example of a configuration of a sensor element 101 included in the gas sensor 100. FIG. 3 is a block diagram illustrating an example of a control device 90. It is to be noted that the sensor element 101 has an elongated rectangular parallelepiped shape, the longitudinal direction (the right-left direction of FIG. 2) of the sensor element 101 is the front-back direction, and the depth direction (the up-down direction of FIG. 2) of the sensor element 101 is the up-down direction. Also, the width direction (the direction perpendicular to the front-back direction and the up-down direction) is the right-left direction. The structure of the gas sensor as illustrated in FIG. 1 is well-known, and is described in WO 2013/005491, for instance.

As illustrated in FIG. 1, the gas sensor 100 includes the sensor element 101, a protective cover 130 that protects the front end side of the sensor element 101, a sensor assembly body 140 including a connector 150 electrically connected to the sensor element 101, and a control device 90 (see FIG. 3). As illustrated, the gas sensor 100 is mounted, for instance, on a pipe 190 such as an exhaust gas pipe of a vehicle, and is used to measure the specific gas concentration, such as $NO_x$, $NH_4$, or $O_2$, contained in an exhaust gas provided as a measurement-object gas. In the present embodiment, the gas sensor 100 is to measure an NOx concentration as a specific gas concentration.

The protective cover 130 includes a bottomed cylindrical inner-side protective cover 131 that covers the front end of the sensor element 101, and a bottomed cylindrical outer-side protective cover 132 that covers the inner-side protective cover 131. In the inner-side protective cover 131 and the outer-side protective cover 132, multiple holes are formed for allowing a measurement-object gas to flow into the protective cover 130. A sensor element chamber 133 is formed as the space surrounded by the inner-side protective cover 131, and the front end of the sensor element 101 is disposed in the sensor element chamber 133.

The sensor assembly body 140 includes a element sealing body 141 that seals and fixes the sensor element 101, a nut 147 and an outer tube 148 mounted on the element sealing body 141, and a connector 150 which is in contact with and electrically connected to connector electrodes (only the later-described heater connector 71 is illustrated in FIG. 2), the connector electrodes being formed on the surface (up-down surface) of the rear end of the sensor element 101 and not illustrated.

The element sealing body 141 includes a tubular main metal fittings 142, a tubular inner tube 143 coaxially welded and fixed to the main metal fittings 142, ceramic supporters 144a to 144c, green pellets 145a, 145b, and a metal ring 146 which are sealed in through holes inwardly of the main metal fittings 142 and the inner-tube 143. The sensor element 101 is located on the central axis of the element sealing body 141, and penetrates the element sealing body 141 in the front-back direction. In the inner-tube 143, a reduced diameter section 143a for pressing the green pellet 145b in the central axial direction of the inner tube 143, and a reduced diameter section 143b for pressing the ceramic supporters 144a to 144c, the green pellets 145a, 145b via the metal ring 146 forward are formed. The green pellets 145a, 145b are compressed between the main metal fittings 142, the inner tube 143, and the sensor element 101 by a pressing force from the reduced diameter sections 143a, 143b, thus the green pellets 145a, 145b seal between the sensor element chamber 133 within the protective cover 130 and space 149 within the outer tube 148, as well as fix the sensor element 101.

The nut 147 is coaxially fixed to the main metal fittings 142, and a male screw section is formed on the outer circumferential surface. The male screw section of the nut 147 is inserted in a fixing member 191 which is welded to the pipe 190 and includes a female screw section on the inner circumferential surface. Thus, the gas sensor 100 is fixed to the pipe 190 with the front end of the sensor element 101 and the protective cover 130 of the gas sensor 100 projecting into the pipe 190.

The outer tube 148 covers the surroundings of the inner tube 143, the sensor element 101, and the connector 150, and multiple lead wires connected to the connector 150 are drawn from the rear end to the outside. The lead wires 155 are electrically connected to the electrodes (described later) of the sensor element 101 via the connector 150. The gap between the outer tube 148 and the lead wires 155 is sealed with a rubber stopper 157. The space 149 within the outer tube 148 is filled with a reference gas (air in the present embodiment). The rear end of the sensor element 101 is disposed in the space 149.

As illustrated in FIG. 2, the sensor element 101 is a element having a laminated body in which six layers, a first substrate layer 1, a second substrate layer 2, a third substrate layer 3, a first solid electrolyte layer 4, a spacer layer 5, and a second solid electrolyte layer 6 are laminated in that order in the drawing view from the lower side, the layers each being an oxygen ion conductive solid electrolyte layer such as zirconia ($ZrO_2$). Also, the solid electrolyte forming these six layers is extremely airtight. Such sensor element 101 is manufactured, for instance, by performing predetermined processing and printing a circuit pattern on each of ceramic green sheets corresponding to the layers, layering the sheets, and further firing and integrating the sheets.

At one leading end (the left side of FIG. 2) of the sensor element 101, between the lower surface of the second solid electrolyte layer 6 and the upper surface of the first solid electrolyte layer 4, a gas introduction port 10, a first diffusion rate control section 11, a buffer space 12, a second diffusion rate control section 13, a first internal space 20, a third diffusion rate control section 30, a second internal space 40, a fourth diffusion rate control section 60, and a third internal space 61 (measurement chamber) are adjacently formed in a manner allowing communication with each other in that order.

The gas introduction port 10, the buffer space 12, the first internal space 20, the second internal space 40, and the third internal space 61 are internal space of the sensor element 101, the internal space being provided in a manner in which the spacer layer 5 is bored, and having the upper part, the lower part, and the lateral part demarcated by the lower surface of the second solid electrolyte layer 6, the upper surface of the first solid electrolyte layer 4, and the lateral surface of the spacer layer 5, respectively.

The first diffusion rate control section 11, the second diffusion rate control section 13, and the third diffusion rate control section 30 are each provided as two horizontally long slits (its opening has a longitudinal direction in the direction perpendicular to FIG. 2). The fourth diffusion rate control section 60 is provided as one horizontally long slit (its opening has a longitudinal direction in the direction perpendicular to FIG. 2) which is formed as the gap with the lower surface of the second solid electrolyte layer 6. It is to be noted that the section from the gas introduction port 10 to the third internal space 61 is also referred to as the measurement-object gas flow section.

An air introduction layer 48 is provided between the upper surface of the third substrate layer 3 and the lower surface of the first solid electrolyte layer 4. The air introduction layer 48 is a porous body comprised of ceramics such as alumina, for instance. The air introduction layer 48 has an inlet section 48c at the rear end face, and the inlet section 48c is exposed to the rear end face of the sensor element 101. The inlet section 48c is exposed to the space 149 of FIG. 1 (see FIG. 1). A reference gas for measuring the NOx concentration is introduced into the air introduction layer 48 through the inlet section 48c. The reference gas is air (the atmosphere in the space 149 of FIG. 1) in the present embodiment. Also, the air introduction layer 48 is formed so as to cover the reference electrode 42. The air introduction layer 48 gives a predetermined diffusion resistance to the reference gas introduced through the inlet section 48c, and introduces the reference gas to the reference electrode 42.

The reference electrode 42 is an electrode formed in a manner to be interposed between the upper surface of the third substrate layer 3 and the first solid electrolyte layer 4, and as described above, the surroundings of the electrode is provided with the air introduction layer 48. The reference electrode 42 is directly formed on the upper surface of the third substrate layer 3, and all but the portion of the reference electrode 42 in contact with the upper surface of the third substrate layer 3 is covered by the air introduction layer 48. Also, as described later, it is possible to measure the oxygen concentration (oxygen partial pressure) in each of the first internal space 20, the second internal space 40, and the third internal space 61 using the reference electrode 42. The reference electrode 42 is formed as a porous cermet electrode (for instance, a cermet electrode composed of Pt and $ZrO_2$). Without being particularly limited to this, the reference electrode 42 has a length of, for instance, 0.2 to 2 mm in the front-back direction, a width of, for instance, 0.2 to 2.5 mm in the right-left direction, and a thickness of, for instance, 5 to 30 mm.

In the measurement-object gas flow section, the gas introduction port 10 is a part opened to the external space, and a measurement-object gas is designed to be taken into the sensor element 101 from the external space through the gas introduction port 10. The first diffusion rate control section 11 is a section that gives a predetermined diffusion resistance to the measurement-object gas taken through the gas introduction port 10. The buffer space 12 is space which is provided for introducing the measurement-object gas, which has been introduced by the first diffusion rate control section 11, to the second diffusion rate control section 13.

The second diffusion rate control section 13 is a section that gives a predetermined diffusion resistance to the measurement-object gas which is introduced from the buffer space 12 to the first internal space 20. When the measurement-object gas is introduced from the outside of the sensor element 101 into the first internal space 20, the measurement-object gas quickly taken to the inside of the sensor element 101 through the gas introduction port 10 by the pressure variation (pulsation of the exhaust pressure when the measurement-object gas is an exhaust gas of an automobile) of the measurement-object gas in the external space is not directly introduced to the first internal space 20, but a concentration variation of the measurement-object gas is cancelled through the first diffusion rate control section 11, the buffer space 12, and the second diffusion rate control section 13, then the measurement-object gas is introduced to the first internal space 20. Consequently, the concentration variation of the measurement-object gas introduced to the first internal space 20 is almost negligible. The first internal space 20 is provided as space for adjusting the oxygen partial pressure in the measurement-object gas introduced through the second diffusion rate control section 13. Such oxygen partial pressure is adjusted by the operation of a main pump cell 21.

The main pump cell 21 is an electrochemical pump cell including an inner side pump electrode 22 having a ceiling electrode section 22a which is provided on substantially the entire lower surface of the second solid electrolyte layer 6 facing the first internal space 20; an outer side pump electrode 23 provided in a manner which allows exposure to the external space (the sensor element chamber 133 of FIG. 1) in a region, corresponding to the ceiling electrode section 22a, of the upper surface of the second solid electrolyte layer 6; and the second solid electrolyte layer 6 interposed between these electrodes.

The inner side pump electrode 22 is formed across the upper and lower solid electrolyte layers (the second solid electrolyte layer 6 and the first solid electrolyte layer 4) which demarcate the first internal space 20, and the spacer layer 5 which provides the lateral wall. Specifically, the ceiling electrode section 22a is formed in the lower surface of the second solid electrolyte layer 6 which provides the ceiling surface of the first internal space 20, a bottom electrode section 22b is directly formed in the upper surface of the first solid electrolyte layer 4 which provides the bottom surface, a lateral electrode section (not illustrated) is formed in the lateral wall surface (inner surface) of the spacer layer 5 constituting the both side wall sections of the first internal space 20 so that the ceiling electrode section 22a and the bottom electrode section 22b are connected, and these sections are disposed in a structure as a tunnel form at the disposition position of the lateral electrode section.

The inner side pump electrode 22 and the outer side pump electrode 23 are each formed as a porous cermet electrode (for instance, a cermet electrode composed of Pt containing 1% of Au and $ZrO_2$). It is to be noted that the inner side pump electrode 22 in contact with the measurement-object gas is formed using a material having a weakened reducing ability against the NOx content in the measurement-object gas.

In the main pump cell 21, a desired pump voltage Vp0 is applied between the inner side pump electrode 22 and the outer side pump electrode 23 to cause a pump current Ip0 to flow in the positive direction or the negative direction between the inner side pump electrode 22 and the outer side pump electrode 23, thereby making it possible to draw the oxygen in the first internal space 20 out to the external space, or draw the oxygen in the external space into the first internal space 20.

Also, in order to detect the oxygen concentration (oxygen partial pressure) in the atmosphere in the first internal space 20, an electrochemical sensor cell, specifically, an oxygen partial pressure detection sensor cell 80 for main pump control is provided, which includes the inner side pump electrode 22, the second solid electrolyte layer 6, the spacer layer 5, the first solid electrolyte layer 4, and the reference electrode 42.

The oxygen concentration (oxygen partial pressure) in the first internal space 20 is found by measuring a voltage V0 in the oxygen partial pressure detection sensor cell 80 for main pump control. In addition, the pump current Ip0 is controlled by performing feedback control on the pump voltage Vp0 of a variable power supply 25 so that the voltage V0 is constant. Thus, the oxygen concentration in the first internal space 20 can be maintained at a predetermined constant value.

The third diffusion rate control section 30 is a section that gives a predetermined diffusion resistance to the measurement-object gas for which the oxygen concentration (oxygen partial pressure) is controlled by the operation of the main pump cell 21 in the first internal space 20, and introduces the measurement-object gas into the second internal space 40.

The second internal space 40 is provided as space for further adjusting the oxygen partial pressure of a measurement-object gas by an auxiliary pump cell 50, the gas having been introduced through the third diffusion rate control section 30 after the oxygen concentration (oxygen partial pressure) is adjusted in advance in the first internal space 20. Consequently, the oxygen concentration in the second internal space 40 can be maintained constant with high accuracy, thereby making it possible to measure the NOx concentration with high accuracy by the gas sensor 100.

The auxiliary pump cell 50 is an auxiliary electrochemical pump cell including an auxiliary pump electrode 51 having a ceiling electrode section 51a provided on substantially the entire lower surface of the second solid electrolyte layer 6 facing the second internal space 40; the outer side pump electrode 23 (is not restricted to the outer side pump electrode 23, but an appropriate electrode outside of the sensor element 101 suffices); and the second solid electrolyte layer 6.

Such auxiliary pump electrode 51 is disposed in the second internal space 40 in a structure as a tunnel form similar to that of the inner side pump electrode 22 provided in the first internal space 20 mentioned earlier. Specifically, the ceiling electrode section 51a is formed for the second solid electrolyte layer 6 which provides the ceiling surface of the second internal space 40, a bottom electrode section 51b is directly formed on the upper surface of the first solid electrolyte layer 4 which provides the bottom surface of the second internal space 40, and a lateral electrode section (not illustrated) connecting the ceiling electrode section 51a and the bottom electrode section 51b is formed on each of both wall surfaces of the spacer layer 5 which provides the lateral wall of the second internal space 40, and has a structure of a tunnel form. It is to be noted that similarly to the inner side pump electrode 22, the auxiliary pump electrode 51 is also formed using a material having a weakened reducing ability against the NOx content in the measurement-object gas.

In the auxiliary pump cell 50, it possible to draw the oxygen in the atmosphere in the second internal space 40 out to the external space, or draw the oxygen in the external space into the second internal space 40 by applying a desired voltage Vp1 across the auxiliary pump electrode 51 and the outer side pump electrode 23.

In addition, in order to control the oxygen partial pressure in the atmosphere in the second internal space 40, an electrochemical sensor cell, specifically, an oxygen partial pressure detection sensor cell 81 for auxiliary pump control is provided, which includes the auxiliary pump electrode 51, the reference electrode 42, the second solid electrolyte layer 6, the spacer layer 5, and the first solid electrolyte layer 4.

It is to be noted that the auxiliary pump cell 50 performs pumping with a variable power supply 52 for which the voltage is controlled based on an voltage V1 detected by the oxygen partial pressure detection sensor cell 81 for auxiliary pump control. Thus, the oxygen partial pressure in the atmosphere in the second internal space 40 is controlled at a low partial pressure which has essentially no effect on the measurement of NOx.

Along with this, a pump current Ip1 is used for controlling the voltage V0 of the oxygen partial pressure detection sensor cell 80 for main pump control. Specifically, the pump current Ip1 is inputted to the oxygen partial pressure detection sensor cell 80 for main pump control as a control signal, and the voltage V0 is controlled so that the gradient of the oxygen partial pressure of the measurement-object gas introduced from the third diffusion rate control section 30 into the second internal space 40 is always controlled at a constant level. When the oxygen partial pressure detection sensor cell 80 for main pump control is used as a NOx sensor, the oxygen concentration in the second internal space 40 is maintained at a constant value of approximately 0.001 ppm by the function of the main pump cell 21 and the auxiliary pump cell 50.

The fourth diffusion rate control section 60 is a section that gives a predetermined diffuse resistance to the measurement-object gas for which the oxygen concentration (oxygen partial pressure) is controlled by the operation of the auxiliary pump cell 50 in the second internal space 40, and introduces the measurement-object gas to the third internal space 61. The fourth diffusion rate control section 60 has a function of limiting the amount of NOx flown into the third internal space 61.

The third internal space 61 is provided as space for performing processing related to measurement of the nitrogen oxide (NOx) concentration in a measurement-object gas, the gas having been introduced through the fourth diffusion rate control section 60 after the oxygen concentration (oxygen partial pressure) is adjusted in advance in the second internal space 40. The measurement of the NOx concentration is performed by the operation of a pump cell 41 for measurement mainly in the third internal space 61.

The pump cell 41 for measurement measures the NOx concentration in a measurement-object gas in the third internal space 61. The pump cell 41 for measurement is an electrochemical pump cell including a measurement electrode 44 directly provided on the upper surface of the first solid electrolyte layer 4 facing the third internal space 61, the outer side pump electrode 23, the second solid electrolyte layer 6, the spacer layer 5, and the first solid electrolyte layer 4. The measurement electrode 44 is a porous cermet electrode. The measurement electrode 44 also functions as a NOx reducing catalyst which reduces NOx present in the atmosphere in the third internal space 61.

The pump cell 41 for measurement can draw oxygen generated by decomposition of nitrogen oxide in the atmosphere of the surroundings of the measurement electrode 44, and can detect the amount of generation as a pump current (pump current for concentration detection) Ip2.

Also, in order to detect the oxygen partial pressure in the surroundings of the measurement electrode 44, an electrochemical sensor cell, specifically, an oxygen partial pressure detection sensor cell 82 for measurement pump control is provided, which includes the first solid electrolyte layer 4, the measurement electrode 44, and the reference electrode 42. A variable power supply 46 is controlled based on an voltage V2 detected by the oxygen partial pressure detection sensor cell 82 for measurement pump control.

The measurement-object gas introduced into the second internal space 40 arrives at the measurement electrode 44 of the third internal space 61 through the fourth diffusion rate control section 60 in a situation where the oxygen partial pressure is controlled. The nitrogen oxide in the measurement-object gas in the surroundings of the measurement electrode 44 is reduced ($2NO \rightarrow N_2+O_2$), and oxygen is generated. The generated oxygen is pumped by the pump cell 41 for measurement, and at that time, a voltage Vp2 of the variable power supply 46 is controlled so that the voltage V2 detected by the oxygen partial pressure detection sensor cell 82 for measurement pump control is maintained at a constant level. The amount of oxygen generated in the surroundings of the measurement electrode 44 is proportional to the concentration of the nitrogen oxide in the measurement-object gas, thus the nitrogen oxide concentration in the measurement-object gas is calculated using the pump current Ip2 in the pump cell 41 for measurement.

Also, an electrochemical Vref detection sensor cell 83 includes the second solid electrolyte layer 6, the spacer layer 5, the first solid electrolyte layer 4, the third substrate layer 3, the outer side pump electrode 23, and the reference electrode 42. The oxygen partial pressure in the measurement-object gas outside the sensor is detectable by a voltage Vref obtained by the Vref detection sensor cell 83.

In addition, an electrochemical reference gas adjustment pump cell 84 includes the second solid electrolyte layer 6, the spacer layer 5, the first solid electrolyte layer 4, the third substrate layer 3, the outer side pump electrode 23, and the reference electrode 42. The reference gas adjustment pump cell 84 performs pumping by carrying an oxygen pumping current Ip3 caused by a voltage Vp3 applied by a power supply circuit connected between the outer side pump electrode 23 and the reference electrode 42. Thus, the reference gas adjustment pump cell 84 pumps oxygen from the space (the sensor element chamber 133 of FIG. 1) in the surroundings of the outer side pump electrode 23 to the surroundings of the reference electrode 42.

In the gas sensor 100 having such a configuration, a measurement-object gas having an oxygen partial pressure maintained at a constant low value (a value essentially having no effect on the measurement of NOx) all the time is provided to the pump cell 41 for measurement by operating the main pump cell 21 and the auxiliary pump cell 50. Thus, the NOx concentration in the measurement-object gas can be found based on the pump current Ip2 which is carried by pumping out oxygen with the pump cell 41 for measurement, the oxygen being substantially proportional to the concentration of the NOx in the measurement-object gas and generated by reduction of the NOx.

In addition, the sensor element 101 includes a heater unit 70 that has a function of temperature adjustment through heating the sensor element 101 and maintaining the temperature in order to enhance the oxygen ion conductivity of the solid electrolyte. The heater unit 70 includes a heater connector electrode 71, a heater 72, a through hole 73, a heater insulation layer 74, a pressure diffusion hole 75, and a lead wire 76.

The heater connector electrode 71 is an electrode formed in a manner to allow connection to the lower surface of the first substrate layer 1. It is possible to supply electric power to the heater unit 70 from the outside by connecting the heater connector electrode 71 to an external power supply.

The heater 72 is an electrical resistor formed in a manner to be interposed vertically between the second substrate layer 2 and the third substrate layer 3. The heater 72 is connected to the heater connector electrode 71 via the lead wire 76 and the through hole 73, is heated by supply of electric power from the outside through the heater connector electrode 71, and performs heating and temperature maintenance of the solid electrolyte forming the sensor element 101.

Also, the heater 72 is embedded across the entire area from the first internal space 20 to the third internal space 61, and can adjust the entire sensor element 101 to a temperature which causes the solid electrolyte to be activated.

The heater insulation layer 74 is an insulation layer formed on the upper and lower surfaces of the heater 72, the insulation layer including porous alumina composed of an insulator such as alumina. The heater insulation layer 74 is formed for the purpose of obtaining electrical insulation between the second substrate layer 2 and the heater 72 and electrical insulation between the third substrate layer 3 and the heater 72.

The pressure diffusion hole 75 is a section provided to penetrate the third substrate layer 3 and the air introduction layer 48, and is formed for the purpose of reducing the increase of an internal pressure in association with temperature rise in the heater insulation layer 74.

It is to be noted that the variable power supplies 25, 46, 52 illustrated in FIG. 2 are actually connected to electrodes via lead wires (not illustrated) formed in the sensor element 101 and the connector 150 and the lead wires 155 of FIG. 1.

As illustrated in FIG. 3, the control device 90 is a well-known microprocessor including a CPU 92 and a memory 94. The control device 90 receives input of the voltage V0 detected by the oxygen partial pressure detection sensor cell 80 for main pump control, the voltage V1 detected by the oxygen partial pressure detection sensor cell 81 for auxiliary pump control, the voltage V2 detected by the oxygen partial pressure detection sensor cell 82 for measurement pump control, the voltage Vref detected by the Vref detection sensor cell 83, the current Ip0 detected by the main pump cell 21, the current Ip1 detected by the auxiliary pump cell 50 and the pump current Ip2 detected by the pump cell 41 for measurement. In addition, the control device 90 outputs a control signal to the variable power supply 25 of the main pump cell 21, the variable power supply 52 of the auxiliary pump cell 50, and the variable power supply 46 of the pump cell 41 for measurement. Also, the control device 90 performs control so that a pulse voltage is outputted to the reference gas adjustment pump cell 84 from a power supply circuit which is not illustrated.

The control device 90 performs feedback control on the pump voltage Vp0 of the variable power supply 25 so that the voltage V0 reaches a target voltage V0*. Thus, the pump current Ip0 is changed according to the concentration of the oxygen contained in the measurement-object gas, eventually the air-fuel ratio (A/F) of the measurement-object gas. Therefore, the control device 90 can calculate the oxygen concentration and A/F of the measurement-object gas based on the pump current Ip0.

In addition, the control device 90 performs feedback control on the voltage Vp1 of the variable power supply 52 so that the voltage V1 reaches a target voltage V1* (in other words, so that the oxygen concentration of the second internal space 40 reaches a predetermined low oxygen concentration which has essentially no effect on the measurement of NOx). It is to be noted that the target voltage V1* may be set in consideration of the voltage drop in the reference electrode 42 due to the oxygen pumping control. Along with this, the control device 90 sets the target voltage V0* of the voltage V0 based on the pump current Ip1. Consequently, the gradient of the oxygen partial pressure is always constant in the measurement-object gas which is introduced from the third diffusion rate control section 30 to the second internal space 40.

Furthermore, the control device 90 performs feedback control on the voltage Vp2 of the variable power supply 46 so that the voltage V2 reaches a target voltage V2* (in other words, so that the concentration of oxygen generated due to reduction of the nitrogen oxide in the measurement-object gas in the third internal space 61 is essentially zero), and calculates a nitrogen oxide concentration in the measurement-object gas based on the pump current Ip2. It is to be noted that the target voltage V2* may be set in consideration of the voltage drop in the reference electrode 42 due to the oxygen pumping control.

The function of the reference gas adjustment pump cell 84 will be described in the following. The measurement-object gas is introduced from the sensor element chamber 133 illustrated in FIG. 1 to the measurement-object gas flow section, such as the gas introduction port 10, of the sensor element 101. In contrast, the reference gas (air) in the space 149 illustrated in FIG. 1 is introduced to the air introduction layer 48 of the sensor element 101. Then, the sensor element chamber 133 and the space 149 are partitioned by the sensor assembly body 140 (particularly, the green pellets 145a, 145b), and sealed so that gas does not flow through each other. However, when the pressure of the measurement-object gas is temporarily increased, a small amount of the measurement-object gas may enter the space 149. As a consequence, when the oxygen concentration in the surroundings of the reference electrode 42 is temporarily reduced, the reference potential, which is the potential of the reference electrode 42, is changed. Thus, a voltage relative to the reference electrode 42, for instance, the voltage V2 of the oxygen partial pressure detection sensor cell 82 for measurement pump control is changed, and the accuracy of detection of the NOx concentration in the measurement-object gas is decreased. The reference gas adjustment pump cell 84 has the function of decreasing such reduction in the accuracy of detection. The control device 90 causes the oxygen pumping current Ip3 to flow by applying a pulse voltage as the voltage Vp3 across the reference electrode 42 and the outer side pump electrode 23 of the reference gas adjustment pump cell 84, thereby performing oxygen pumping control to pump oxygen from the surroundings of the outer side pump electrode 23 into the surroundings of the reference electrode 42, the pulse voltage (see FIG. 4) being repeatedly turned ON and OFF with a predetermined period (for instance, 10 msec). Consequently, as described above, when the measurement-object gas temporarily reduces the oxygen concentration in the surroundings of the reference electrode 42, the reduced oxygen can be compensated, and reduction in the accuracy of detection of the NOx concentration can be decreased.

Figure 6:
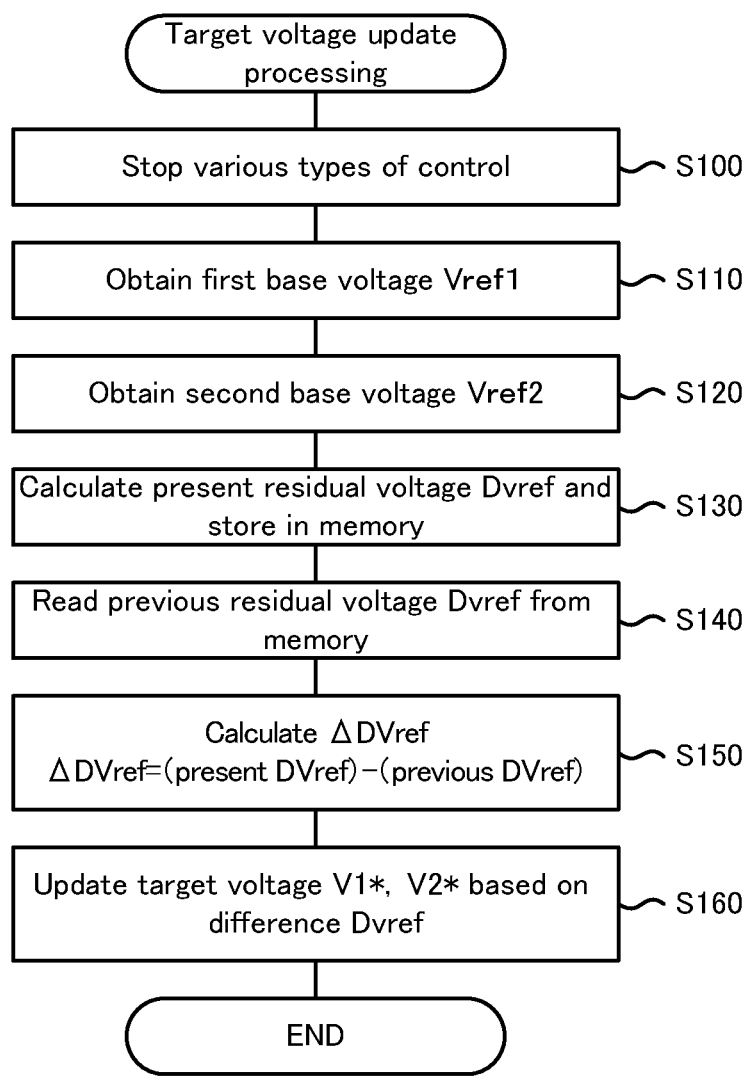
FIG. 6 is a flowchart illustrating an example of target voltage update processing.

Next, the target voltage update processing performed by the control device 90 will be described in the following. The target voltage update processing is the processing to update the target voltages V1*, V2*. The flowchart of the target value update processing is illustrated in FIG. 6. The target voltage update processing is started every predetermined time (for instance, every 50 hours or every 100 hours). However, the target voltage update processing may be started when an operator inputs a start command to the target voltage update processing.

When the processing is started, the CPU 92 of the control device 90 stops various types of control (S100). Specifically, the CPU 92 stops the feedback control of the pump voltage Vp0 to cause the voltage V0 to reach the target voltage V0*, the feedback control of the pump voltage Vp1 to cause the voltage V1 to reach the target voltage V1*, the feedback control of the pump voltage Vp2 to cause the voltage V2 to reach the target voltage V2* and the oxygen pumping control to pump oxygen into the reference electrode 42.

Figure 5:
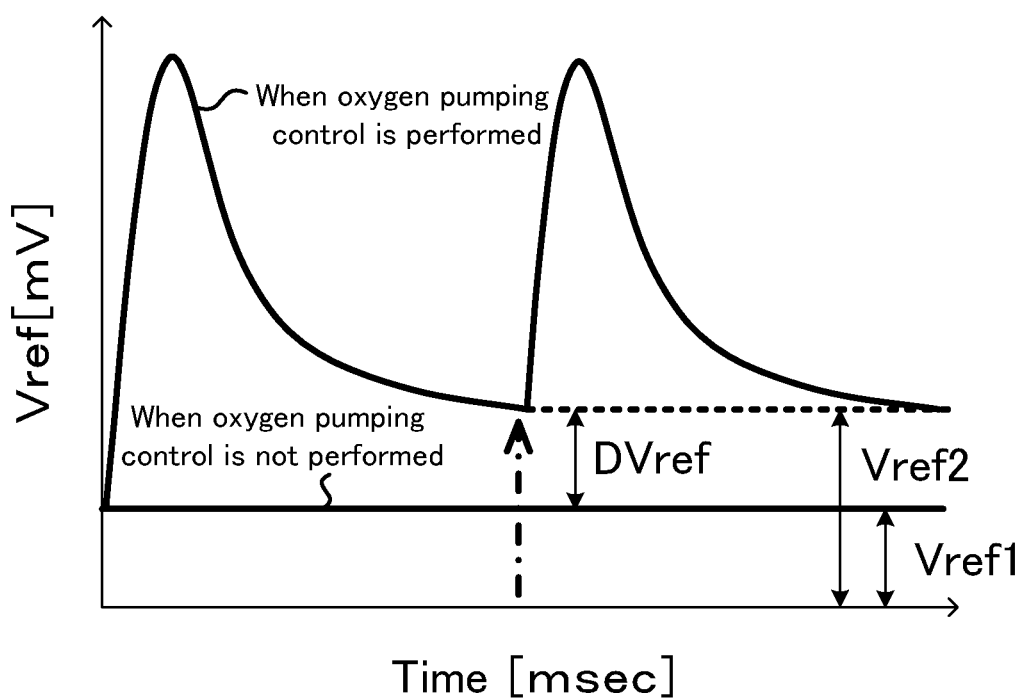
FIG. 5 is an explanatory graph illustrating an example of change with time in a voltage Vref.

Next, the CPU 92 obtains a first base voltage Vref1 across the reference electrode 42 and the outer side pump electrode 23 when the oxygen pumping control is not performed (S110). Specifically, after allowing a zero state of the voltage Vp3 to continue for a predetermined time (for instance, approximately 100 times the period of the pulse voltage), the CPU 92 reads the voltage Vref, and stores it as the first base voltage Vref1 in the memory 94. The first base voltage Vref1 is the voltage when substantially no effect of the pulse voltage is observed, and as illustrated in FIG. 5, the voltage has a constant value regardless of the time elapsed. The first base voltage Vref1 includes an electromotive force based on the oxygen concentration difference between the reference gas and the measurement-object gas.

Figure 4:
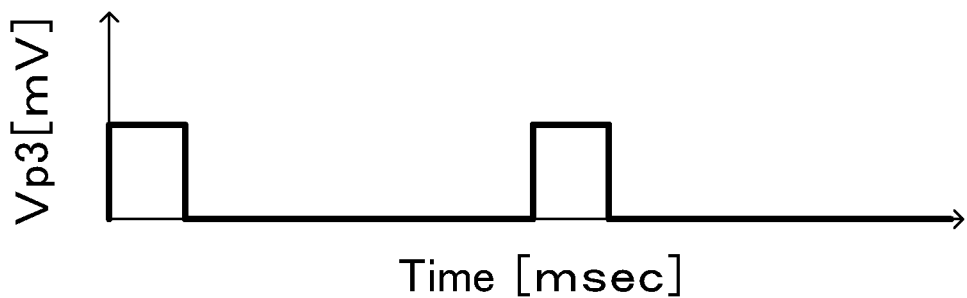
FIG. 4 is an explanatory graph illustrating an example of change with time in a voltage Vp3.

Next, the CPU 92 obtains a second base voltage Vref2 across the reference electrode 42 and the outer side pump electrode 23 when the oxygen pumping control is performed (S120). When the pulse voltage in FIG. 4 is applied to the voltage Vp3 across the reference electrode 42 and the outer side pump electrode 23, the voltage Vref detected by the Vref detection sensor cell 83 is changed as illustrated in FIG. 5. Specifically, when the pulse voltage for the voltage Vp3 is set ON, the voltage Vref gradually rises accordingly, and when the pulse voltage for the voltage Vp3 is set OFF, the voltage Vref gradually falls accordingly. During the period since the pulse voltage is set OFF until the pulse voltage is set ON next, the voltage Vref approximately converges to a predetermined voltage. The CPU 92 reads the voltage Vref (converged voltage) immediately before (see the arrow of a dashed line in FIG. 5) the pulse voltage is set ON next time after the pulse voltage is set OFF, and stores the voltage Vref as the second base voltage Vref2 in the memory 94. The second base voltage Vref2 includes a voltage (voltage drop) in addition to the electromotive force based on the oxygen concentration difference between the reference gas and the measurement-object gas, the voltage being obtained by multiplying the resistance of the reference electrode 42 by the oxygen pumping current which flows through the reference electrode 42.

It is to be noted that when the first and second base voltages Vref1, Vref2 are obtained, respective oxygen concentrations of the measurement-object gas should be the same. For instance, in the case where the measurement-object gas is exhaust gas of an internal combustion, respective oxygen concentrations contained in the exhaust gas are the same when no fuel is supplied to the internal combustion, thus the first and second base voltages Vref1, Vref2 are obtained when no fuel is supplied.

Next, the CPU 92 calculates the present residual voltage DVref, and stores it in the memory 94 (S130). Specifically, the CPU 92 calculates the present residual voltage DVref by subtracting the first base voltage Vref1 from the second base voltage Vref2, and stores the present residual voltage DVref in the memory 94. The residual voltage DVref is probably equal to the voltage (voltage drop) obtained by multiplying the resistance of the reference electrode 42 by the oxygen pumping current which flows through the reference electrode 42.

Next, the CPU 92 reads the previous residual voltage DVref from the memory 94 (S140), and calculates the difference ΔDVref by subtracting the previous residual voltage DVref from the present residual voltage DVref (S150). The difference ΔDVref is probably equal to the difference between the present voltage drop and the previous voltage drop. In other words, it may be stated that the difference ΔDVref is a voltage that reflects the amount of resistance change when the reference electrode 42 degrades with time from the previous time to the present time and the resistance of the reference electrode 42 changes. It is to be noted that for the first time of the target voltage update processing, the difference ΔDVref can be considered to be zero because the previous residual voltage DVref is not stored in the memory 94.

Next, the CPU 92 updates the target voltages V1*, V2* based on the difference ΔDVref (S160), and completes the present routine. Specifically, the CPU 92 calculates the present target voltages V1*, V2* by reflecting the difference ΔDVref on the previous target voltages V1*, V2*.

Subsequently, the CPU 92 resumes the various types of control which have been stopped in S100. Specifically, the CPU 92 resumes the oxygen pumping control, performs feedback control on the voltage Vp1 so that the voltage V1 reaches the target voltage V1* after being updated, and performs feedback control on the voltage Vp2 so that the voltage V2 reaches the target voltage V2* after being updated. In addition, the CPU 92 reads the pump current Ip2 at the same timing as the timing of measurement of the second base voltage Vref2, in other words, at the timing immediately before the pulse voltage is set ON next time after the pulse voltage is set OFF, and calculates the NOx concentration in the measurement-object gas based on the pump current Ip2.

The pump current Ip2 used for determining the NOx concentration is the current which flows through the pump cell 41 for measurement when the variable power supply 46 (the voltage Vp2) of the pump cell 41 for measurement is controlled so that the voltage V2 reaches the target voltage V2*. The voltage V2 includes the electromotive force based on the oxygen concentration difference between the surroundings of the measurement electrode 44 and the surroundings of the reference electrode 42, the thermal electromotive force between the measurement electrode 44 and the reference electrode 42, and the value (voltage drop) obtained by multiplying the resistance of the reference electrode 42 by the oxygen pumping current through the reference electrode 42. Although the thermal electromotive force hardly changes with time, the voltage drop changes with time because the reference electrode 42 degrades with time, and the resistance changes. When the voltage V2 is controlled at a constant level, increase in the voltage drop reduces the electromotive force based on the oxygen concentration difference between the surroundings of the measurement electrode 44 and the surroundings of the reference electrode 42, thereby causing the accuracy of detection of NOx concentration to be reduced. However, in the present embodiment, as described above, the target voltage V2* is updated based on the residual voltage DVref corresponding to the voltage drop. Thus, when the voltage V2 is controlled so as to reach the target voltage V2*, the electromotive force based on the oxygen concentration difference between the surroundings of the measurement electrode 44 and the surroundings of the reference electrode 42 is not reduced, and the accuracy of detection of NOx concentration is improved.

The voltage V1 is the value of measurement of the potential difference between the reference electrode 42 and the auxiliary pump electrode 51, thus is effected by the oxygen pumping current which flows through the reference electrode 42. Therefore, update of the target voltage V1* of the voltage V1 based on the residual voltage DVref enables the oxygen concentration of the second internal space 40 to be controlled with high accuracy at a predetermined low oxygen concentration which has essentially no effect on the measurement of NOx. The voltage V1 includes the electromotive force based on the oxygen concentration difference between the surroundings of the auxiliary pump electrode 51 and the surroundings of the reference electrode 42, the thermal electromotive force between the auxiliary pump electrode 51 and the reference electrode 42, and the value (voltage drop) obtained by multiplying the resistance of the reference electrode 42 by the oxygen pumping current through the reference electrode 42.

Here, the corresponding relationship between the components of the present embodiment and the components of the present invention will be clarified. A laminated body in which six layers are laminated in the order given below in the present embodiment corresponds to the laminated body in the present invention, the six layers being the first substrate layer 1, the second substrate layer 2, the third substrate layer 3, the first solid electrolyte layer 4, the spacer layer 5, and the second solid electrolyte layer 6. The reference electrode 42 corresponds to the reference electrode, the measurement electrode 44 corresponds to the measurement electrode, the outer side pump electrode 23 corresponds to the measurement-object gas side electrode, and the CPU 92 of the control device 90 corresponds to the control device and the calculation device.

In the gas sensor 100 of the present embodiment described in detail above, although the oxygen concentration of the reference gas is reduced, for instance, when the measurement-object gas enters the surroundings of the reference electrode 42, the reduction in the oxygen concentration of the reference gas can be prevented by performing the oxygen pumping control. In addition to the voltage based on the oxygen concentration difference between the surroundings of the measurement electrode 44 and the surroundings of the reference electrode 42, the voltage V2 across the reference electrode 42 and the measurement electrode 44 also includes the voltage drop obtained by multiplying the resistance of the reference electrode 42 by the oxygen pumping current which flows through the reference electrode 42 at the time of the oxygen pumping control. The voltage drop is probably equal to the residual voltage DVref which is the difference between the first base voltage Vref1 and the second base voltage Vref2, the first base voltage Vref1 across the reference electrode 42 and the outer side pump electrode 23 when the oxygen pumping control is not performed, the second base voltage Vref2 across the reference electrode 42 and the outer side pump electrode 23 when the oxygen pumping control is performed. Here, since the NOx concentration in the measurement-object gas is corrected based on the residual voltage DVref, it is possible to prevent reduction in the accuracy of detection of the NOx concentration due to degradation with time of the reference electrode 42.

Since the oxygen pumping control is performed using the pulse voltage, and the pump current Ip2 and the second base voltage Vref2 are measured in a period in which the pulse voltage if OFF, it is possible to reduce the effect of the voltage used for the oxygen pumping control on the measurement of the pump current Ip2 and the second base voltage Vref2. Particularly, because the pump current Ip2 and the second base voltage Vref2 are measured at the timing immediately before the pulse voltage is set ON next time in a period in which the pulse voltage is OFF, such effect can be further reduced.

In addition, the difference ΔDVref is probably equal to the difference between the present voltage drop and the previous voltage drop. Specifically, it may be stated that the difference ΔDVref is the voltage that reflects the amount of resistance change when the reference electrode 42 degrades with time from the previous time to the present time and the resistance of the reference electrode 42 changes. Thus, the target voltages V1*, V2* can be appropriately set by correcting the target voltages V1*, V2* based on the difference.

The present invention is not limited to the above-described embodiments, and can be carried out by various modes as long as they belong to the technical scope of the invention.

For instance, in the embodiment described above, the NOx concentration is corrected by reflecting the difference ΔDVref on the previous target voltages V1*, V2*. However, without being limited to this particularly, the NOx concentration may be corrected, for instance, by reflecting the difference ΔDVref on detected voltages V1, V2 without updating the target voltages V1*, V2*.

Figure 7:
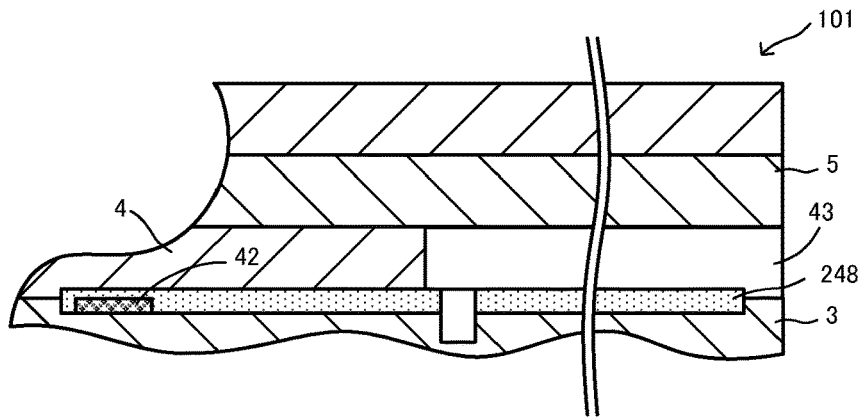
FIG. 7 is a cross-sectional schematic view illustrating the structure of the surroundings of an air introduction layer 248.

In the embodiment described above, an air introduction layer 248 illustrated in FIG. 7 may be used instead of the air introduction layer 48. The air introduction layer 248 is exposed to a reference gas introduction space 43 which is obtained by boring a rear portion of the first solid electrolyte layer 4. The air introduction layer 248 is designed to allow air to enter through the exposed portion.

Figure 8:
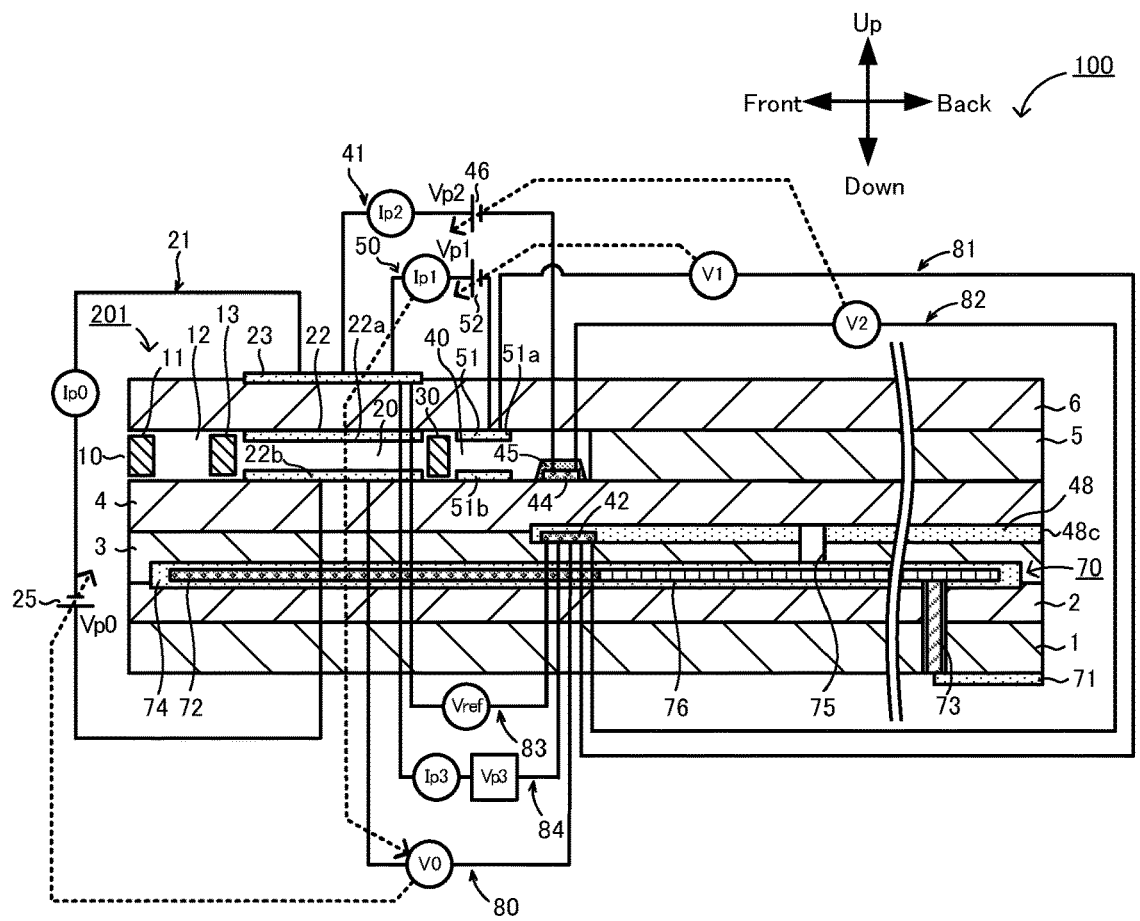
FIG. 8 is a cross-sectional schematic view of a sensor element 201 in a modification.

In the embodiment described above, the sensor element 101 of the gas sensor 100 includes the first internal space 20, the second internal space 40, the third internal space 61. However, without being limited to this, the sensor element 101 may not include the third internal space 61 as in a sensor element 201 in FIG. 8, for instance. In the sensor element 201 according to a modification illustrated in FIG. 8, between the lower surface of the second solid electrolyte layer 6 and the upper surface of the first solid electrolyte layer 4, the gas introduction port 10, the first diffusion rate control section 11, the buffer space 12, the second diffusion rate control section 13, the first internal space 20, the third diffusion rate control section 30, and the second internal space 40 are formed adjacently in a manner in which the components communicate with each other in that order. The measurement electrode 44 is disposed on the upper surface of the first solid electrolyte layer 4 in the second internal space 40. The measurement electrode 44 is covered with a fourth diffusion rate control section 45. The fourth diffusion rate control section 45 is a film comprised of a ceramic porous body, such as alumina ($Al_2O_3$). Similarly to the fourth diffusion rate control section 60 in the embodiment described above, the fourth diffusion rate control section 45 has a function of limiting the amount of NOx which flows in the measurement electrode 44. In addition, the fourth diffusion rate control section 45 also serves as a protective film for the measurement electrode 44. The ceiling electrode section 51*a* of the auxiliary pump electrode 51 is formed up to just above the measurement electrode 44. Even with such a configuration of the sensor element 201, similarly to the embodiment described above, the NOx concentration can be detected by the pump cell 41 for measurement. In that case, the surroundings of the measurement electrode 44 serve as a measurement chamber. It is to be noted that the same component as in FIG. 2 is labeled with the same symbol in FIG. 8.

In the embodiment described above, the reference electrode 42 is directly formed on the upper surface of the third substrate layer 3. However, without being limited to this, the reference electrode 42 may be directly formed on the lower surface of the first solid electrolyte layer 4, for instance.

In the embodiment described above, the case has been described in which the NOx concentration contained in the measurement-object gas is measured. However, without being limited to the NOx concentration, for instance, the ammonia concentration contained in the measurement-object gas may be measured using the gas sensor 100. In that case, the inner side pump electrode 22 in the first internal space 20 is made to contain metal having a catalytic function which promotes oxidation of ammonia. The ammonia contained in the measurement-object gas is oxidized in the first internal space 20, and is transformed to NO. The NO, after being transformed, is introduced into the third internal space 61 serving as a measurement chamber through the second internal space 40. Thus, measurement of the ammonia concentration is basically made by the same principle as used for measurement of the NOx concentration.

Figure 9:
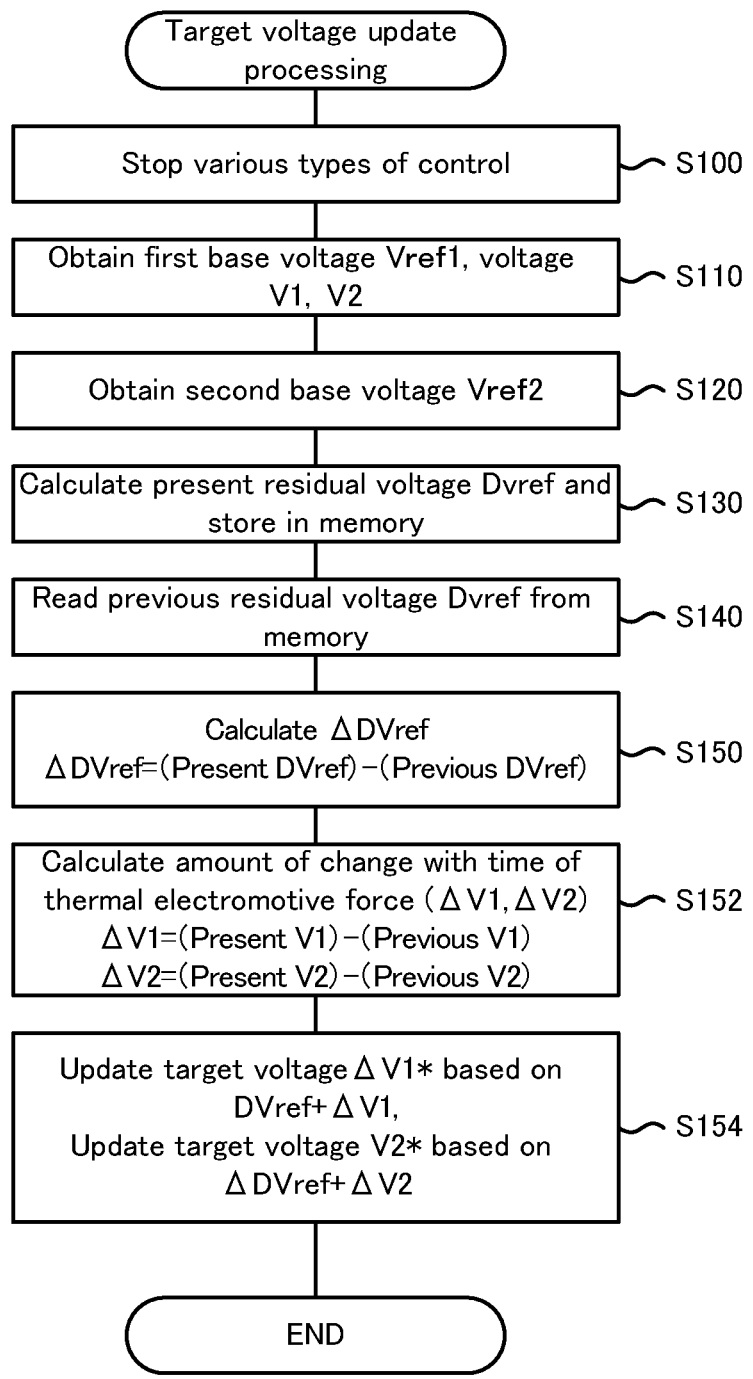
FIG. 9 is a flowchart illustrating another example of the target voltage update processing.

In the embodiment described above, the NOx concentration may be further corrected based on the amount of change with time in the thermal electromotive force. An example is illustrated by the flowchart in FIG. 9. The thermal electromotive force may refer to the thermal electromotive force generated by the temperature difference between the measurement electrode 44 and the reference electrode 42 and the thermal electromotive force generated by the temperature difference between the auxiliary pump electrode 51 and the reference electrode 42. In the flowchart illustrated in FIG. 9, the processing in S100 to S150 of the embodiment described above is performed. However, in S110, the CPU 92 also obtains the voltages V1, V2 when the various types of control are stopped and the oxygen pumping control is not performed. After S150, the CPU 92 calculates the differences ΔV1, ΔV2 (S152). The difference ΔV1 is the value calculated by subtracting the voltage V1 obtained in the previous S110 from the voltage V1 obtained in the present S110. The difference ΔV1 is probably equal to the difference amount (the amount of change with time) between the present time and the previous time in the thermal electromotive force generated by the temperature difference between the measurement electrode 44 and the reference electrode 42. The difference ΔV2 is the value calculated by subtracting the voltage V2 obtained in the previous S110 from the voltage V2 obtained in the present S110. The difference ΔV2 is probably equal to the difference amount (the amount of change with time) between the present time and the previous time in the thermal electromotive force generated by the temperature difference between the auxiliary pump electrode 51 and the reference electrode 42. It is to be noted that for the first time of the target voltage update processing, the differences ΔV1, ΔV2 are considered to be zero. Next, the CPU 92 updates the target voltage V1* based on the sum of the difference ΔDVref and the difference ΔV1 as well as updates the target voltage V2* based on the sum of the difference ΔDVref and the difference ΔV2 (S154), then completes the present routine. Specifically, the CPU 92 calculates the present target voltage V1* by reflecting (for instance, adding) the difference ΔDVref and the difference ΔV1 on the previous target voltage V1* as well as the present target voltage V2* by reflecting the difference ΔDVref and the difference ΔV2 on the previous target voltage V2*. According to the flowchart in FIG. 9, the same effect as provided by the embodiment described above is obtained, and in addition, even when the thermal electromotive force changes with time, the NOx concentration is detected in consideration of the change with time, thus it is possible to further prevent reduction with time in the accuracy of detection of a specific gas concentration.

In the embodiment described above, the difference ΔDVref is set to the difference between the present ΔDVref and the previous ΔDVref. However, the difference ΔDVref may be the difference between the present ΔDVref and the initial time (the initial timing of start of use) ΔDVref. In that case, the present target voltages V1*, V2* may be calculated by reflecting (for instance, adding) the difference ΔDVref on the initial time target voltages V1*, V2*. Also, in the flowchart of FIG. 9, In addition to the setting of the difference ΔDVref to the difference between the present ΔDVref and the initial ΔDVref, the differences ΔV1, ΔV2 may be the values obtained by subtracting the initial (the initial timing of start of use) voltages V1, V2 from the present voltages V1, V2. The present target voltages V1*, V2* may be calculated by reflecting the difference ΔDVref and the difference ΔV1 on the initial target voltage V1 and reflecting the difference ΔDVref and the difference ΔV2 on the initial target voltage V2.

What is claimed is:

1. A gas sensor comprising:
   a laminated body which has a plurality of laminated oxygen ion conductive solid electrolyte layers and is inwardly provided with a measurement-object gas flow section, the measurement-object gas flow section being a section into and through which a measurement-object gas is introduced and flows;
   a reference electrode which is disposed inside the laminated body, and a reference-gas introduction section open outward of the laminated body and introducing a reference gas, the reference gas serving as a reference for detection of a specific gas concentration in the measurement-object gas;
   a measurement electrode provided on an inner circumferential surface of a measurement chamber of the measurement-object gas flow section;
   a measurement-object gas side electrode disposed on the laminated body such that the measurement-object-gas side electrode comes into contact with the measurement-object gas;
   a control device that performs oxygen pumping control to pump oxygen from surroundings of the measurement-object gas side electrode into surroundings of the reference electrode; and
   a calculation device that, during execution of the oxygen pumping control, measures a pump current for concentration detection when oxygen originating from the specific gas is pumped out from surroundings of the measurement electrode so that a voltage across the reference electrode and the measurement electrode reaches a target voltage, and calculates the concentration of the specific gas in the measurement-object gas based on the pump current for concentration detection,
   wherein the calculation device is configured to correct the concentration of the specific gas in the measurement-object gas based on a difference between a first base voltage and a second base voltage, the first base voltage being the voltage across the reference electrode and the measurement-object gas side electrode when the oxygen pumping control is not performed, the second base voltage being the voltage across the reference electrode and the measurement-object gas side electrode when the oxygen pumping control is performed.

2. The gas sensor according to claim 1,
wherein the oxygen pumping control device performs the oxygen pumping control by applying a voltage repeatedly turned ON and OFF across the measurement-object gas side electrode and the reference electrode, and
the calculation device measures the pump current for concentration detection and the second base voltage in a period in which the voltage repeatedly turned ON and OFF in the oxygen pumping control is OFF.

3. The gas sensor according to claim 2,
wherein the calculation device measures the pump current for concentration detection and the second base voltage at a timing in the period in which the voltage repeatedly turned ON and OFF in the oxygen pumping control is OFF, the timing being immediately before the voltage repeatedly turned ON and OFF is set to ON.

4. The gas sensor according to claim 1,
wherein when measuring the pump current for concentration detection, the calculation device corrects the target voltage based on a difference amount between a difference of the first base voltage and the second base voltage at a present time and a difference of the first base voltage and the second base voltage in a past time, and the calculation device measures the pump current for concentration detection when oxygen originating from the specific gas is pumped out from the surroundings of the measurement electrode so that the target voltage after being corrected is achieved.

5. The gas sensor according to claim 1,
wherein the calculation device is configured to further correct the concentration of the specific gas in the measurement-object gas based on an amount of change with time in a thermal electromotive force.

* * * * *